United States Patent [19]

Carlson et al.

[11] Patent Number: 5,157,207
[45] Date of Patent: Oct. 20, 1992

[54] MODIFIED PLANT CONTAINING A BACTERIAL INSCULANT

[75] Inventors: Peter S. Carlson, Alexandria, Va.;
Jed W. Fahey, Columbia, Md.;
Jeffrey L. Flynn, Greenwell Springs, La.

[73] Assignee: Crop Genetics International, Hanover, Md.

[21] Appl. No.: 475,869

[22] Filed: Feb. 6, 1990

[51] Int. Cl.$^5$ .................. A01H 3/00; A01H 5/00; A01N 63/00

[52] U.S. Cl. .................. 800/200; 47/57.6; 47/DIG. 9; 71/76; 424/93 D; 435/843; 800/DIG. 55; 800/DIG. 56; 800/DIG. 57; 800/DIG. 58; 935/64

[58] Field of Search ........ 800/200; 47/57.6, DIG. 11, 47/58; 71/76; 935/64

[56] References Cited

U.S. PATENT DOCUMENTS

| | | | |
|---|---|---|---|
| 4,061,488 | 12/1977 | Mann | 47/57.6 |
| 4,456,684 | 6/1984 | Weller et al. | 435/34 |
| 4,479,936 | 10/1984 | Vandenbergh et al. | 424/93 |
| 4,647,533 | 3/1987 | Weller et al. | 435/29 |

FOREIGN PATENT DOCUMENTS 8703303 6/1987 World Int. Prop. O. .

OTHER PUBLICATIONS

Ullstrup 1977 In Corn and Corn Inprovement; Agronomy Series No. 18; Sprague (ed); A3A Publisher pp. 391–401, 421, 429–432, 444–445.
Leath et al. 1988 In Alfalfa and Alfalfa Improvement; Agronomy Series No. 29; Hanson et al. (ed) AsA Publisher pp. 621–623, 659–661.
Sinclair 1984 Compendium of Soybean Diseases; APS Publisher; pp. 1–3 and 5–6.
Steindl, 1961 In Sugarcan Diseases of the World: vol. 1; Elsevier Publisher pp. 433–459.
Johnson et al. 1988 Phytopath 78 (12, Part I): 1540 (Abstract #220).
Clay 1989 Mycol. Res. 92 (1):1–12.
Davis et al. 1984 Plant Disease 68 (12):1095–1097.
Davis et al. 1984 J. System, Bacterial, 34:107–117.
Dalrymple, D. G., Development and Spread of High-Yielding Rice Varieties in Developing Countries, Bureau for Science and Technology, Agency for International Development, Washington, D.C. (1986), pp. 1, 9, 11–12, 17–20, 22, 25 and 30–31.
Herbert, C. D., Growth Regulation in Cereals-Chance or Design? Chemical Manipulation of Crop Growth and Development, J. S. McLaren ed., Butterworth Scientific (London 1982), pp. 315–327.

*Primary Examiner*—Elizabeth C. Weimar
*Assistant Examiner*—P. Rhodes
*Attorney, Agent, or Firm*—Finnegan, Henderson, Farabow, Garrett & Dunner

[57] ABSTRACT

A method for the production of a plant of reduced stature is provided comprising the introduction of a bacterial cell into a seed or a plant, the bacterial cell being capable of replicating in the plant and of inducing a reduction in plant stature. A seed and a plant modified by introduction of such a bacterial cell are also provided.

6 Claims, No Drawings

MODIFIED PLANT CONTAINING A BACTERIAL INSCULANT

FIELD OF THE INVENTION

The present invention relates to a modified seed and a modified plant, respectively, into each of which a bacterial cell is affirmatively introduced, the modified seed and modified plant being capable of developing into a modified plant of reduced stature. A method of producing a plant of reduced stature is also provided as well as a method of introducing a bacterial cell into a seed.

BACKGROUND OF THE INVENTION

One of the goals of commercial agriculture is to increase the yield of crops. Yield increases have been obtained, for example, by reducing plant stature. By reducing the stature of plants, relatively less of the plant's biomass becomes involved in the production of stem and leaves and relatively more of the plant's biomass becomes involved in grain production. Furthermore, by reducing the stature of plants, the resistance of plants to lodging, i.e., falling over, is increased. Lodging is undesirable because the resultant flattened crop and secondary growth make harvesting difficult. Moreover, when plants lodge, the grain becomes dirty and wet and rots, thereby necessitating grain drying and causing delay in harvesting and loss of yield.

Throughout the history of agronomy, plant breeders have produced plants of reduced stature by selection and breeding, or by induction of mutation through irradiation or chemical means, as discussed in Dalrymple, D. G., DEVELOPMENT AND SPREAD OF HIGH-YIELDING RICE VARIETIES IN DEVELOPING COUNTRIES, Bureau for Science and Technology, Agency for International Development, Washington, D.C. (1986). The production of such plants of reduced stature, in accordance with the conventional methods, entails selection of appropriate parent stock, manipulation of the parent stock by hybridization or mutation, propagation of progenies, and further selection and breeding. Such processes are time-consuming and expensive.

Plant growth and development are also known to be regulated by the external application of plant growth regulators, such as hormones and other chemicals. Responses to such chemical applications, however, are variable, as discussed in Herbert, C. C., Growth Regulation in Cereals—Chance or Design?, in CHEMICAL MANIPULATION OF CROP GROWTH AND DEVELOPMENT, J. S. McLaren, ed., Butterworth Scientific (London 1982), pp. 315-327. Moreover, application of chemicals for purposes of regulating plant growth has to be performed in accordance with a precise schedule, without much allowance for flexibility.

The plants of reduced stature produced by conventional breeding means, such as those described above, are normally adapted to growth and cultivation under a specific set of environmental conditions. Because of the elaborate processes involved in breeding and adaptation, however, only a limited number of dwarf varieties of a particular crop are customarily adapted for cultivation in a given region. This often leads to planting of either a monoculture or a limited variety of crops by a given farmer. It is a concern among commercial farmers, therefore, that should disease strike the one or few varieties cultivated, the entire crop will be decimated. It would be desirable, therefore, to provide an easier, less expensive and less time-consuming method of producing a plant of reduced stature so that more varieties of a crop can be planted at any given time.

Microorganisms have been known to affect plant growth and development. Certain types of microorganisms, such as hybrid agricultural-chemical-producing endosymbiotic microorganisms, colonize the interior of plants and provide useful agricultural chemicals, such as pesticides, to the plants. Certain microbial endophytes are capable of inducing enhanced resistance in a host to phytopathogens.

Furthermore, pathogenic strains of *Clavibacter xyli* that inhabit sugar cane and bermudagrass and cause stunting disease in these plants have been reported. In Davis, M. J. et al. [*J. System. Bacteriol.* 34:107-117 (1984)], ratoon stunting disease of sugarcane is attributed to infection by *Clavibacter xyli* subsp. xyli. The stunting effect of this infection was associated with significant yield losses. In Davis, M. J. and Augustin, B. J. [*Plant Disease* 68:1095-1097 (1984)], a bermudagrass stunting disease is attributed to *Clavibacter xyli* subsp. cynodontis. The diseased grass reportedly appeared as unsightly circular patches of chlorotic and dying grass. The bacterial species causing ratoon stunting disease and that causing bermudagrass stunting disease were determined to be distinct from each other because each was able to induce a disease condition in its natural host but not in the natural host of the other. Yet, on the other hand, both bacteria could be found growing in the xylem vessels of both hosts, as stated in Davis et al. (1984). Subspecies of *Clavibacter xyli*, therefore, have been known to cause disease only in their natural hosts.

In addition to bacterial cells, fungal endophytes have also been known to cause stunting in infected plants, particularly, in infected grasses as discussed in Clay, K., *Mycol. Res.* 92:1-12 (1989). Fungal endophytes, however, often produce toxic alkaloids that are not appropriate for agricultural crops. In particular, for purposes of producing plants that yield edible seeds such as rice, infection by fungal endophytes are associated with certain disadvantages. For example, plants that are infected with fungal endophytes can become sterile and not produce seeds at all, or the fungal spores and toxic materials produced by the fungal endophytes, such as alkaloids, may find their way into the seeds, thus making the seeds unsatisfactory as food sources. Hence, the use of fungal endophytes to produce a reduction in plant stature is not desirable.

The present inventors have recognized that there exists a need for an easy, inexpensive and efficient method of producing a plant of reduced stature, particularly, that of an agricultural crop. They have recognized that it would be desirable if a microorganism can be found that can be introduced into a nonnatural host to produce a plant of reduced stature and yet, would not produce any harmful or undesirable side effects associated with stunting due to a natural infection of such a microorganism in its natural host. Such a microorganism should not produce any toxic compounds such as alkaloids and should not sporulate or grow in the seeds of the host so as not to contaminate, for example, the seeds of cereal crops. Infection of plants by a microorganism that can produce the above-described effect would be an easy, efficient and inexpensive method of producing plants of reduced stature.

SUMMARY OF THE INVENTION

It is, therefore, an object of the present invention to provide a method of producing a plant of reduced stature in a manner that overcomes the disadvantages of conventional techniques.

It is a further object of the present invention to provide a method of producing a plant of reduced stature in a manner that is easy, inexpensive and efficient.

It is another object of the present invention to provide a plant of reduced stature by use of a microorganism.

It is another object of the present invention to provide a plant of reduced stature by use of a microorganism that will not affect the yield of the plant, that will not transmit the microorganism to the seed of the plant and that will not result in any toxic chemicals in the seed.

It is yet another object of the present invention to provide a modified seed containing a microorganism, the modified seed being capable of developing into a plant of reduced stature, and the microorganism having the characteristics described above.

It is still another object of the present invention to provide a modified plant containing a microorganism, the modified plant being capable of developing into a plant of reduced stature, the microorganism also having the characteristics described above.

In accomplishing these objects, there has been provided, in accordance with one aspect of the present invention, a method for the production of a plant of reduced stature comprising introducing a bacterial cell into a seed of the plant to produce a modified seed, and developing the modified seed into a modified plant, the bacterial cell being capable of replicating in the modified plant to produce a reduction in stature of said modified plant.

In accordance with a further aspect of the present invention, there has been provided a method for the production of a plant of reduced stature comprising introducing a bacterial cell into a plant to produce a modified plant, and developing said modified plant, the bacterial cell having the characteristics described above, and the plant is a dicotyledonous plant or a monocotyledonous plant such as a cereal crop.

In accordance with another aspect of the present invention, there has been provided a method for introducing bacterial cells into a seed by adding the bacterial cells to a biologically compatible liquid carrier to form a suspension, impregnating the seeds with the suspension, and removing the excess carrier from the seeds, to form a viable seed comprising a viable bacterial cell.

In accordance with a another aspect of the present invention, there has been provided a modified seed comprising a seed of a plant and a bacterial cell introduced into the seed, the modified seed being capable of growing into a modified plant comprising the bacterial cell, and the bacterial cell being capable of replicating in the modified plant to produce a reduction in stature of the modified plant.

In accordance with another aspect of the present invention, there has been provided a modified plant comprising a plant and bacterial cell introduced into the plant, the bacterial cell having the characteristics as described above, and the plant is a dicotyledonous plant or a monocotyledonous plant such as a cereal crop.

Further objects, features and advantages of the present invention will become apparent from the following detailed description. It should be understood, however, the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Reference will now be made in detail to the presently preferred embodiments of the invention, which, together with the following examples, serve to explain the principles of the invention.

It has been discovered that a seed of a plant can be modified by introduction of a bacterial cell into the seed with limited or no injury to the seed. In the context of the present invention, the seed modified in this manner is capable of growing into a modified plant in which the bacterial cell can replicate and produce a reduction in stature of the modified plant. In addition, applicants have discovered that a plant itself can also be modified by introduction of a bacterial cell into the plant with limited or no injury to the plant, the bacterial cell is capable of replicating in the plant and producing a modified plant of reduced stature, the plant being a dicotyledonous plant or a monocotyledonous plant such as a cereal crop.

Furthermore, applicants have discovered a method of producing a plant of reduced stature by introduction of a bacterial cell into a seed to produce a modified seed, or into a plant to produce a modified plant, the modified seed, the modified plant and the bacterial cell each having the characteristics described above. The process of introduction of a bacterial cell into a seed or plant can be accomplished by any acceptable technique that will preserve the viability of the seed or the plant and of the bacterial cell.

Within the content of the present invention, a "reduction in stature of a plant" refers to an effect caused by the affirmative introduction of a bacterial cell into a seed or a plant, whereby the height of the mature plant measured from the ground to the highest visible ligule ("hvl") is reduced from the average height of a similar plant in the field which is not so infected.

The bacterial cell that is suitable for use in the present invention belongs to a species of bacteria that is capable of replicating in the interior tissues of a plant and of effecting, either directly or indirectly, a reduction in plant stature. Under normal field conditions, the bacterial cell within the present invention does not ordinarily inhabit the seed or the plant into which the bacterial cell is introduced. Such a bacterial cell can be a gram-positive bacterium, a gram-negative bacterium or a species of actinomycetes. The bacterial cell can be unmodified or modified, either by genetic engineering techniques to incorporate foreign genes or by mutagenesis. In a preferred embodiment, the bacterial cell is an unmodified species of either Corynebacteria, Clavibacter, Pseudomonas, Xanthomonas or Erwinia, the corynebacteria and clavibacters being as defined in Davis M. J. et al. (1984), loc. cit. In a particularly preferred embodiment, the bacterial cell is an unmodified strain of *Clavibacter xyli*. In a most preferred embodiment, the bacterial cell is an unmodified *Clavibacter xyli* subspecies cynodontis (hereafter "Cxc"). A preferred strain of *Clavibacter xyli* subsp. cynodontis is one that is on deposit at *American Type Culture Collection*, 12301 Parklawn Drive, Rockville, Md. 20852, U.S.A., under Accession No. 33973. In an alternative embodiment, Cxc can be isolated from infected bermudagrass, a natural host species, from areas where Cxc is known to be found, e.g., in Louisiana.

As used herein, the term "genetically engineered" or similar terms refer to bacterial cells that have been manipulated by human intervention to delete or rearrange DNA from those cells, or to add to those cells DNA or RNA, including DNA or RNA from a different organism, by conventional techniques including, but not limited to, recombinant DNA, recombinant RNA, cell fusion, protoplast fusion, conjugation, plasmid transfer, transformation, transfection and transduction.

Known protoplast and spheroplast fusion techniques are described in D. A. Hopwood, "Genetic Studies With Bacterial Protoplasts," *Ann. Rev. Microbiol.*, 35:237-72 (1981), and in R. L. Weiss, *J. Bacteriol.*, 128:668-70 (1976), both of which are specifically incorporated herein by reference. Selection of a technique by which the fusion hybrids of the present invention may be formed will generally be within the capabilities of one of ordinary skill in the art based on the above-referenced scientific literature.

In general, the fusion procedure involves the removal of the cell wall from the bacteria to be fused, fusion of the bacterial cells in a fusion-inducing medium, such as polyethylene glycol, and regeneration of the cell wall about the fusion hybrids. Fusion and regeneration of the cell wall are conducted at low temperatures so that rates of expressible genetic recombination are favored in relation to rates of enzymatic destruction of genetic material in the newly formed hybrids.

Following initial formation of fusion hybrids, the genetic make-up of the bacteria population is relatively unstable for a period of 2 or 3 days, during which much genetic recombination apparently occurs. During this time period, those stable fusion hybrids capable of manifesting the one or more selectable traits are selected.

In a preferred embodiment of the present invention, the bacterial cell that is suitable for use in the present invention is capable of growing in the vascular tissues of a plant, e.g., the xylem. It is preferable that the bacterial cell be nonsporulating and it is most preferable that the bacterial cell is not transmittable to the seed of the modified plant.

Virtually any type of seeds may be used in the present invention, provided they are seeds and they produce plants both of which the bacterial cell of the present invention does not ordinarily inhabit or infect under normal field conditions. These include seeds of both monocotyledonous and dicotyledonous plants that may be useful for agronomic, horticultural, or ornamental purposes. A preferred group of plants that provide seeds that are suitable for the present invention is either dicotyledonous plants or monocotyledonous plants such as cereal crops. The cereal crops include, but are not limited to, wheat, barley, rye, rice, and oats as well as corn, millet, and sorghum. Particularly preferred seeds are those for rice. Among the monocotyledonous plants, the seeds of which are suitable for use in the present invention, a cereal crop or plant that is capable of utilizing either the C3 (Calvin) or the C4 (Hatch-Slack) photosynthetic pathway is preferred.

In another embodiment of the present invention, the plant itself is modified by introduction of a bacterial cell. In such an instance, the plant is one that the bacterial cell of the present invention does not ordinarily inhabit or infect under normal field conditions. Preferably, the plant is either a monocotyledonous plant such as a cereal crop, or a dicotyledonous plant. Among the cereal crops that are suitable for use herein, wheat, barley, rye, oats, as well as sorghum, corn, millet are preferred, and rice is particularly preferred.

In carrying out the method of producing a plant of reduced stature of the present invention, a bacterial cell is affirmatively introduced into a seed to produce a modified seed that can develop into a modified plant of reduced stature, or into a plant to produce a modified plant of reduced stature. Further, in carrying out the method of the present invention, the bacterial cells and the seeds or plants that are suitable for use are bacterial cells that are not found in the seeds or plants sought to be modified, absent affirmative inoculation of such bacterial cells.

The terms "affirmative introduction of the bacterial cells into the seed" or "impregnation of seeds," within the context of the present invention, mean to actively or positively introduce the bacterial cells to the inside of the outer, protective seed coat, i.e., the pericarp or the testa. Moreover, in certain instances, for example, in the case of corn seeds, at least for *Clavibacter xyli* subsp. cynodontis, the microorganisms must be in the embryo itself for the resulting plant to be colonized.

For purposes of affirmatively introducing bacterial cells into the seeds, the bacterial cell of the present invention may be micro-encapsulated with a suitable nutrient source. Such nutrient sources include, for example, dehydrated culture medium; components of a culture medium such as cysteine and bovine serum albumin; and complex carbohydrate or amino acid sources, such as milk, starch or yeast extract. The nutrient source and the bacterial cell can be both encapsulated by freeze-drying, spray-drying, liposome entrapment or other conventional techniques.

In one embodiment of the present invention, the bacterial cell is introduced into the seed by wounding the seed and contacting the bacterial cell with the wound. In another embodiment of the present invention, the bacterial cell is introduced into the seed by (1) placing a bacterial cell in a biologically compatible liquid carrier to form a suspension, and (2) impregnating the seeds with the suspension. Preferably, excess suspension or carrier is removed from the seeds, such as by evaporation. This process of introducing bacterial cells into seeds is accomplished in such a way that the viability of both the bacterial cell and the seeds is maintained, so that the seed is capable of germinating and the bacterial cell is capable of replicating in the resulting plant.

The bacterial cell to be introduced into both plants and seeds can be cultured or maintained in any medium that permits growth or sustains viability, respectively. The cell cultures can be concentrated or diluted to obtain the desired density for inoculation into seeds or plants. Preferably, the bacterial cells used herein are derived from cultures that are substantially pure, that is, substantially free of unwanted microorganisms.

The biologically compatible liquid carrier for the bacterial cell, within the present invention, is any liquid in which the bacterial cell can form a suspension and which is not lethal to either the bacterial cell or the seeds. Such a liquid carrier includes water and a water-based buffer, such as phosphate buffered saline. In a preferred embodiment, the biologically compatible liquid carrier comprises a solution of water and a water-soluble gum, which may be natural or synthetic. Such gums include gelatin, sodium alginate, gum ghatti, xanthan gum, karaya gum, Dow-Corning 1944/B polymer, which is a silicone oil from Dow-Corning, polyethylene oxide, Natrolsol TM, which is a hydroxyethyl cellulose from Hercules Chemical Co., tragacanth gum, guar gum, gum arabic, locust bean gum, methylceluose, carboxmethycellulose, starch, and Rhoplex TM B-15, which is an aqueous acrylic emulsion from Rohm & Haas. Particularly preferred gums are methylcellulose, carboxymethycellulose, xanthan gum, and Rhoplex TM. The gums are preferably used in a concentration of from about 0.1% to about 10% weight per volume of water.

The liquid carrier may also contain a buffer, which assists in maintaining the viability of the microorganism, and a surfactant. Suitable surfactants for use herein are, e.g., Tween 20 (polyoxyethylenesorbitan monolaurate), Tween 40 (polyoxyethylenesorbitan monopalmitate), Tween 60 (polyoxyethylenesorbitan monopalmitate), Tween 80 (polyoxyethylenesorbitan monoleate), Tween 85 (polyoxyethylenesorbitan trioleate), Regulaid (polyoxyethylenepolypropoxypropanol and alkyl-2-ethoxy ethanol dihydroxy propane), and Surfel (83% paraffin-based petroleum oil; 15% polyol fatty acid esters and polyethoxylated derivatives and 2% unidentified components). Organic solvents and penetrants such as dimethyl sulfoxide (DMSO) or N,N-dimethyl formamide (DMF), also serve as liquid carriers and promote colonization. Particularly preferred concentrations are 1% DMSO or 3% DMF.

In addition, chemicals such as fungicides can be added to the liquid carrier and used at a concentration that is not lethal to the bacterial cell. For example, *Clavibacter xyli* subsp. cynodontis has been found to tolerate significant levels of certain fungicides.

In an alternative embodiment, the biologically compatible liquid carrier is an organic solvent. In such instances, particularly, when it is desirable that the bacterial cell be dormant, the organic solvent should be substantially anhydrous. Otherwise, the presence of water in the organic solvent can cause the bacterial cell to reenter into an active metabolic state. Dormancy can be induced in the bacterial cell by conventional techniques, e.g., by lyophilization.

Virtually any organic solvent that is not toxic to the seed or to the dormant bacterial cell, and which can maintain the dormancy of the bacterial cell may be used. These include acetone, dichloromethane, trichloromethane (i.e., chloroform), carbon tetrachloride, DMSO, DMF, methanol, ethanol, benzene, n-hexane, cyclohexane, ortho-xylene, meta-xylene, and para-xylene, isopropanol, and n-butanol. Volatile organic solvents are particularly preferred because they have the advantage of being easily evaporated at the end of the process.

Various oils have also been found to be useful as organic solvents. These include oils that are relatively inert and nontoxic to the bacterial cell and the seeds such as vegetable oil, mineral oil, linseed oil, and silicone oil.

The parameters of the impregnation process, including the type of liquid carried, the presence and concentration of surfactants, solvents and penetrants, may be varied and optimized on a case-by-case basis by conventional means. The process of impregnation of seeds with bacterial cells, in the context of the present invention, can be accomplished by any conventional techniques as long as the viability of the seeds and of the bacterial cells is maintained. In an embodiment of the present invention, seeds can be impregnated in a manner described (1) adding beneficial microorganisms to a biologically compatible liquid carrier to form a suspension of the microorganism in the carrier; and (2) impregnating the seeds with the suspension or otherwise introducing the suspension into the seeds.

Preferably, the excess suspension or carrier is removed from the seeds, such as by evaporation. This process is accomplished in such a way that the viability of the microorganisms and the seeds is maintained, so that the seeds are capable of germinating and the microorganisms are capable of colonizing the resulting plant.

The microorganisms can be in any culture medium that permits growth or sustains viability. Preferably, the cultures are substantially pure, that is, substantially free of unwanted microorganisms.

The biologically compatible liquid carrier is any liquid in which the microorganisms can form a suspension and which is not lethal to either the microorganisms or the seeds. This includes water and a water-based buffer, such as phosphate buffered saline. The suspensions are formed by adding cultures of the microorganisms to the liquid carrier and mixing microorganisms with the carrier and by related techniques known to persons skilled in the art.

In a preferred embodiment, the biologically compatible liquid carrier comprises a solution of water and a water-soluble gum. Such gums may be natural or synthetic. They include gelatin, sodium alginate, gum ghatti, xanthan gum, karaya gum, Dow-Corning 1944A/B polymer (a silicone oil made by Dow-Corning), polyethylene oxide, Natrosol TM (a hydroxyethyl cellulose made by Hercules Chemical Co.,), tragacanth gum, guar gum, gum arabic, locust bean gum, methylcellulose, carboxymethylcellulose, starch, and Rhoplex TM B-15 (an aqueous acrylic emulsion made by Rohm & Haas). Methylcellulose, carboxymethylcellulose, xanthan gum, and Rhoplex TM are particularly preferred. These gums appear to act as a drying and preserving agent for the microorganisms as well as binding them to microscopic cracks within the seed or to intracellular spaces. They are preferably used in a concentration from about 0.1% to about 10% weight per volume of water.

After the microorganisms have been impregnated into the seeds, it is preferable that the excess suspension and carrier be removed. When the liquid carrier is an anhydrous organic solvent, drying may be accomplished rapidly at ambient temperature. When the liquid carrier contains water, the seeds are dried and careful selection of the dry-down temperature by means known to those of ordinary skill in the art is beneficial. The drying causes the microorganisms to become dormant. When the gum is used, it appears to act as a matrix in which enough moisture is removed so that the microorganisms become dormant yet enough moisture is maintained so that they remain visible.

The liquid carrier may also contain a buffer, which assists in maintaining the viability of the microorganisms, and surfactants, such as Tween 20 (polyoxyethylenesorbitan monolaurate), Tween 40 (polyoxyethylenesorbitan monopalmitate), Tween 60 (polyoxyethylenesorbitan monostearate), Tween 80 (polyoxyethylenesorbitan monooleate), Tween 85 (polyoxyethylenesorbitan trioleate), Regulaid (polyoxyethylenepolypropoxypropanol and alkyl-2-ethoxy ethanoldihydroxy propane), and Surfel (83% paraffin-based petroleum oil; 15% polyol fatty acid esters and polyethoxylate derivatives and 2% unidentified components). The surfactants aid in permitting the suspension of the microorganisms and the carrier to penetrate microscopic cracks and fissures in the hard, outer seed coat so that the microorganisms end up within the coat. Organic solvents and penetrants such as dimethyl sulfoxide (DMSO) or N,N-dimethyl formamide (DMF), also promote colonization, probably by nature of their unique properties as universal solvents and their ability to reduce surface tension. Particularly preferred concentrations are 1% DMSO or 3% DMF. In addition, chemicals such as fungicides can be added to the liquid carrier, if they are not lethal to the microorganisms. The toxicity of the fungicides can be determined by the person skilled in the art on a case-by-case basis. For example, *Clavibacter xyli* subsp. cynodontis has been found to tolerate significant levels of certain fungicides.

In an alternative embodiment, the biologically compatible liquid carrier is a substantially anhydrous organic solvent. Most organic solvents are toxic to metabolically active microorganisms. In such cases, the microorganisms should be dormant, and the organic solvent should be substantially anhydrous because water could cause microorganisms to reenter the active state. Microorganisms can be made dormant before being added to the solvent by conventional techniques. Lyophilization is preferred.

Virtually any organic solvent, which is nontoxic to the seed or the dormant microorganisms and which maintains the dormancy of the microorganisms, may be used. These include acetone, dichloromethane, trichloromethane (chloroform), carbon tetrachloride, DMSO, DMF, methanol, ethanol, benzene, n-hexane, cyclohexane, ortho-, meta-, and para-xylene, isopropanol, and n-butanol. Volatile organic solvents are particularly preferred because they have the advantage of being easily evaporated at the end of the process.

Various oils have also been found to be useful as organic solvents. These include vegetable, mineral, linseed, and silicone oil. The oils are relatively inert and nontoxic to the microorganisms and the seeds.

The parameters of the impregnation process, including type of liquid carrier, presence and concentration of surfactants, solvents and penetrants, may in light of the specification, be varied on a case-by-case basis depending on the variety of seed or plant, by means known to one of ordinary skill in the art to optimize the impregnation process.

One method of impregnation of seeds that is suitable for use herein comprises mixing a suspension of bacterial cells with the seeds to be impregnated and applying a vacuum, as described, e.g., in Goth, *Plant Disease Reporter*, 50:110-111 (1966), the contents of which are incorporated herein by reference. At the end of the evacuation process, the system is allowed to rapidly repressurize, thereby allowing the suspension to be drawn into the seeds. The degree of the vacuum and the length of time it is applied can be determined by a person skilled in the art in view of the teachings herein. A preferred time period for evacuation is about 40 minutes or less. When this technique is used with a water-based system, the seeds may be presoaked to enhance the ease of penetration by the bacterial cell suspension. It is preferable that some seeds, for example, corn, are presoaked or imbibed overnight for approximately 17 hours or for one day.

A second method of impregnating the seeds in the present invention involves applying the bacterial cell suspension to the seeds or otherwise mixing the seeds and the suspension and applying pressure. The degree of pressure and the length of time it is applied can be determined by a person skilled in the art in view of the teachings herein. In the pressure treatment, any gas may be used but, preferably, $O_2$, $N_2$ or compressed air.

A third technique for impregnation of seeds within the present invention involves forceful injection of a bacterial cell suspension into the seeds. This can be done by any effective technique, e.g., with a needle and syringe, a medical needleless jet injector, or by coating the suspension onto high velocity microprojectiles and propelling projectiles into the seeds with sufficient force to cause them to penetrate the coat, as described, for example, in Klein et al., *Nature*, 327:70-74 (1987), the contents of which are incorporated herein by reference. Forceful injection can also be done by wounding the seed, e.g., by puncturing the seed coat with a solid needle and contacting the wound with the bacterial cell suspension, or by vacuum or pressure infiltration.

Needleless injection is accomplished by propelling a small amount of from about 10 microliters to about 100 microliters of bacterial cells suspended in a liquid carrier through a small jet or orifice under very high pressure. The stream of liquid remains coherent over a short distance and "punctures" a hole for itself in a solid substrate. Any number of these injectors that have been developed for the medical products industry can be used to propel the bacterial cells into the seed or plant tissue according to the methods of the present invention. With the microprojectile technique, it is possible to coat a culture of the bacterial cells directly onto, or place the bacterial cells into the microprojectiles without first suspending them in the biologically compatible liquid carrier.

The carrier need only be applied to the seeds and allowed to remain in contact with the seeds for a period of time sufficient for the carrier to naturally penetrate the seed coat and bring the microorganisms into the seed. For certain embodiments of the invention, it is preferable, but not necessary, to add a finely divided inorganic solid, such as diatomaceous earth, microparticulate glass, or carborundum, to the suspension to cause "cracks" which enhance penetration of the bacterial cell.

After the seeds have been impregnated with the bacterial cell suspension, preferably, the excess suspension and/or carrier is removed. When the liquid carrier contains water or a volatile organic solvent, the water or solvent is allowed to evaporate at ambient temperature before the seeds are stored. The evaporation may, however, be assisted by drying of the seeds in accordance with conventional techniques, the only requirement being that viability of the seeds and of the bacterial cells be maintained. The seeds impregnated with bacterial cells may be planted or otherwise germinated immediately or stored until germination is desirable. If the seeds are stored, it is preferable that they be stored at a controlled level of temperature and humidity. It is within the skill of one of ordinary skill in the art to select the appropriate temperature and humidity for storage to maintain optimum viability.

The introduction of the bacterial cells into seeds may be performed without taking special precautions to prevent seed contamination by undesirable or harmful microorganisms. However, it is preferred that contamination be controlled by treatment of the seeds with fungicides or other conventional seed treatments. Such treatments may be applied, for example, via coating, pelleting, or film-coating, in order to prevent seed or plant damage.

A bacterial cell can also be introduced directly into a plant itself, instead of via the seed, to produce a modified plant in which the bacterial cell can replicate. In a preferred embodiment of the present invention, the bacterial cell does not, under normal field conditions, ordinarily infect or colonize the plant into which the introduction of bacterial cells is desired. The term "affirmative introduction of bacterial cells into a plant" as used herein means to actively or positively introduce the bacterial cells into the interior tissues of a plant, such as the vascular tissues. In practicing the present invention, the bacterial cells can be added to a biologically compatible liquid carrier, as previously described to form a suspension. This bacterial cell suspension can then be used for affirmative introduction into plants, using any conventional techniques that are capable of preserving the viability of the plants and of the bacterial cells. Vacuum and pressure infiltration are most conveniently used with seedlings. Injection with needleless medical injectors, or with microprojectiles is more conveniently done with more mature plants. The technique of needleless injection is described, for example, in Wastie, *Plant Pathology*, 33:61–64 (1984), the contents of which is incorporated herein by reference.

In a further embodiment of the present invention, the bacterial cells are affirmatively introduced into a plant by wounding a plant and contacting the bacterial cells with the wound. A plant can be wounded, for example, by stem stabbing, that is, wounding the plant by means of a sharp instrument. A preferred method of stem stabbing involves the use of a scalpel or other sharp instrument that is first coated with bacterial cells to simultaneously wound and deliver the bacteria into the interior of the plant. In another embodiment of the present invention, the bacterial cells are introduced into the plants by stem injection. "Stem injection" refers to the process of puncturing the stem of a plant by a sharp instrument, e.g., a needle, such as a turberculin intradermal syringe, and gently delivering the bacterial cell in the syringe into the stem.

In a further embodiment of the present invention, the bacterial cells are introduced into plants either by injection into the petiole of a dicotyledonous plant or by deposition onto a previously broken petiole. In still another embodiment, the bacterial cells can be introduced by intercellular infiltration, in which a suspension of bacterial cells is injected into the intercellular spaces of a leaf.

In a particularly preferred embodiment, the plant to be inoculated can be trimmed with clipper blades, for example, either at a low cutting height at about the highest visible ligule ("hvl") or at a high cutting height of about 3 cm above the hvl. Simultaneously, the clipper blades and rice plants can be sprayed with an inoculum of the bacteria, e.g., *Clavibacter xyli* subsp. cynodontis, at a high concentration, e.g., about $1.4 \times 10^{11}$ cfu/ml in phosphate buffered saline ("PBS").

In as yet another embodiment of the present invention, the bacterial cells are introduced into the part of a plant where they are most likely to grow and replicate, such as the vascular tissues. In the case of rice, for example, *Clavibacter xyli* subsp. cynodontis is affirmatively introduced into the xylem of the plant.

A seed can be modified, in the context of the present invention, by impregnating it with bacterial cells in accordance with the methods described above. The modified seed can be allowed to germinate in greenhouse flats and later transplanted to field conditions for development into a modified plant. Similarly, a plant, preferably, a young seedling, can be modified by impregnating it with bacterial cells, under greenhouse conditions, and later transplanted to field conditions.

Colonization of the modified plant by the introduced bacterial cells can be monitored by examination of the stem tissues or by examination of the sap expressed from the stem tissues of such plants by conventional techniques. For example, sap can be expressed from a stem section of the modified plant and examined under phase-contrast microscopy, to determine the presence of the bacterial cells. Alternatively, sap can be expressed and cultured on an agar medium or a in a liquid medium that allows for growth of the bacterial organism. The latter process is generally referred to as "culture indexing." Moreover, a radioimmunoassay or a fluorescent antibody assay can be used to determine colonization. For example, polyclonal antibodies to the bacteria can be induced in laboratory animals such as rabbits. The polyclonal antibodies from the laboratory animals can be labelled with a fluorescein dye for fluorescent antibody assays or can be used with, e.g. goat anti-rabbit antibodies that are radioactively labelled, for radioimmunoassays.

It is to be understood that the application of the teachings of the present invention to a specific problem or environment will be within the capabilities of one having ordinary skill in the art in light of the teachings contained herein. An example of the products of the present invention and processes for their production appears as follows which is illustrative only and is in no sense limiting.

EXAMPLE 1

Introduction of *Clavibacter xyli* subsp. cynodontis into rice plants for production of a modified rice plant of reduced stature.

A trial was established at a commercial rice farm in Leroy, La., in a small leveed field planted to the variety Mercury. A central section of the field large enough to accommodate the trial was cleared of rice and plowed to produce a good seedbed for receiving transplants.

To ensure colonization of *Clavibacter xyli* subsp. cynodontis ("Cxc") in the rice plants, transplants of rice were produced in greenhouse flats, inoculated with Cxc, and subsequently examined for colonization, prior to planting in the field. Seeds of the rice variety Lemont were planted to trays of 1.5 in. pots containing sterilized field soil on May 10. Shortly after germination, benches of trays containing flats were flooded with about 3 in. of water. Cxc organisms were inoculated into the rice plant seedlings by stem stabbing on June 2, using Cxc isolate 123b that was concentrated to over $10 \times 10^{11}$ cfu per ml of phosphate buffered saline ("PBS").

The Cxc isolate 123b was isolated from bermudagrass in the field in Louisiana in the following manner: Stem sections of the bermudagrass were first examined for the presence of Cxc by phase contrast microscopy. Positive samples were selected and sap was expressed from these samples and cultured either on SC agar medium or in SC liquid medium. SC medium consists of 1000 ml distilled water; 17 g cornmeal for liquid medium or 17 g cornmeal agar for agar medium; 8 g papain digest of soy meal; 1 g $K_2HPO_4$; 1 g $KH_2PO_4$; 0.2 g $MgSO_4.7H_2O$; 15 ml of a 0.1% solution, containing about 15 mg of bovine hemin chloride in 0.05 N NaOH; 10 ml of a 20% aqueous solution, containing about 2 g of bovine serum albumin fraction 5; 1.0 ml of a 50% aqueous solution containing about 1 g of cysteine (free base). The Cxc-inoculated media were incubated for 6 days at 28° C. ±3° C.

Twenty days after Cxc inoculation, the Lemont rice plants were randomly selected from inoculated flats. Sap was expressed from parts of selected plants and was examined under phase contrast microscopy to confirm colonization. The following day rice plants were hand-transplanted to plots, each consisting of six rows of plants, with 7 in. between centers and 12 ft. long. An average of 432 plants were planted to each plot, separated by 1.5 ft. alleys from adjacent plots. Cxc-inoculated and noninoculated controls were arranged according to a paired t-test design and replicated six times. The field received a permanent flood directly following transplant and recommended cultural practices for rice production in Louisiana were followed.

Colonization of the rice plants by Cxc was assessed at various intervals during the crop development from randomly selected plants from each plot by either phase-contrast examination of expressed sap or by culture indexing. Stand counts were taken on August 15, from four meter long sections over the middle four rows of each plot. Plant height measurements were taken on July 26 and August 15, respectively, by measuring randomly selected plants per plot from the base to the highest visible ligule ("hvl"). Counts of plants with exposed panicles (heading) were also collected on the latter date.

Growth differences in rice plants between Cxc-inoculated and non-inoculated control plots were noted within a few weeks after transplanting. Rice plants in inoculated plots were substantially shorter than those in control plots on both dates measured, as shown in Table 1. As plants were in late boot to early heading stage of development at the time of the second measurement, the latter could be considered a terminal height. The Cxc-inoculated rice plots produced a 23.5% greater ($p<0.06$) plant stand population than controls.

TABLE 1

Comparison of rice plant growth between Cxc-inoculated and non-inoculated control plots in a field trial at Leroy, Louisiana.

| TREATMENT | PLANT HEIGHT (cm) July 26 | PLANT HEIGHT (cm) August 15 |
|---|---|---|
| Cxc-inoc. | 23.1 | 45.5 |
| Control | 28.4 | 54.4 |
| C.V. | 9.6 | 4.5 |
| % DIFF. | 18.7* | 16.4** |

*($p < 0.05$)
**($p < 0.01$)

Plant development recorded as a percent of the plants with visible panicles on August 15, indicated that inoculated plots were slower to mature, with only 0.3% of plants heading compared to 31.6% in the control. This developmental delay was probably reflected in grain moisture levels at harvest which were 4.7% greater in the Cxc-inoculated plants. Despite the effects on plant height and development, the inoculated plots did not suffer any apparent yield loss, as shown in Table 2.

TABLE 2

Yield comparison between Cxc-inoculated and non-inoculated control plots in the field trial at Leroy, Louisiana.

| TREATMENT | PLOT WT. (g) | YIELD (kg/ha[1]) |
|---|---|---|
| Cxc-inoc. | 1,381 | 4,814 |
| Control | 1,321 | 4,661 |
| C.V. | 6.9 | 6.9 |
| % DIFF | +4.5 ns | +3.3 ns |

[1]Yields corrected for 12% moisture.
ns = not significant

It will be apparent to those skilled in the art that various modifications and variations can be made in the processes and products of the present invention. For example, it is anticipated that the degree of seed and plant colonization by the bacterial cells can be optimized by those skilled in the art, given the teachings of the instant specification. Thus, it is intended that the present invention cover such modifications and variations, provided that they come within the scope of the appended claims and their equivalents.

What is claimed is:

1. A modified rice plant comprising a bacterial inoculant of *Calvibacter xyli* subp. cynodontis.

2. A modified rice plant as claimed in claim 1, wherein said bacterial inoculant is introduced into the plant by a process comprising wounding the plant and contacting the wound with the bacterial inoculant.

3. A modified rice plant as claimed in claim 1, wherein said bacterial inoculant is introduced into the plant by a process comprising contacting a rice seed with the bacterial inoculant followed by germinating said seed to form the modified rice plant.

4. A modified rice plant as claimed in claim 3, wherein said bacterial inoculant is introduced into the plant by a process comprising wounding a rice seed and contacting the wound with the bacterial inoculant followed by germinating said seed to form the modified rice plant.

5. A modified rice plant as claimed in claim 3, wherein said bacterial inoculant is introduced into the plant by a process comprising impregnating a rice seed with the bacterial inoculant followed by germinating said seed to form the modified rice plant.

6. A modified rice plant as claimed in claim 1 wherein the bacterial inoculant inhabits the vascular tissue of the plant.

* * * * *

UNITED STATES PATENT AND TRADEMARK OFFICE
CERTIFICATE OF CORRECTION

PATENT NO. : 5,157,207

DATED : October 20, 1992

INVENTOR(S) : Carlson et al.

It is certified that error appears in the above-identified patent and that said Letters Patent is hereby corrected as shown below:

On the title page, item (54):

In the Title, line 2, change "INSCULANT" to --INOCULANT--.

Signed and Sealed this

Twenty-eighth Day of September, 1993

Attest:

BRUCE LEHMAN

*Attesting Officer*     *Commissioner of Patents and Trademarks*